US010896485B2

(12) United States Patent
Maack

(10) Patent No.: US 10,896,485 B2
(45) Date of Patent: Jan. 19, 2021

(54) FEATURE SUPPRESSION IN DARK FIELD OR PHASE CONTRAST X-RAY IMAGING

(71) Applicant: KONINKLIJKE PHILIPS N.V., Eindhoven (NL)

(72) Inventor: Hanns-Ingo Maack, Norderstedt (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 117 days.

(21) Appl. No.: 16/098,248

(22) PCT Filed: May 4, 2017

(86) PCT No.: PCT/EP2017/060633
§ 371 (c)(1),
(2) Date: Nov. 1, 2018

(87) PCT Pub. No.: WO2017/191247
PCT Pub. Date: Nov. 9, 2017

(65) Prior Publication Data
US 2019/0180416 A1      Jun. 13, 2019

(30) Foreign Application Priority Data

May 4, 2016   (EP) .................................... 16168300

(51) Int. Cl.
*G06T 5/00*       (2006.01)
*G06T 5/50*       (2006.01)
(Continued)

(52) U.S. Cl.
CPC .............. *G06T 5/001* (2013.01); *A61B 6/463* (2013.01); *A61B 6/484* (2013.01); *A61B 6/50* (2013.01);
(Continued)

(58) Field of Classification Search
CPC .. G06T 5/001; G06T 7/74; G06T 7/33; G06T 3/0068; G06T 5/50; G06T 2207/10116;
(Continued)

(56) References Cited

U.S. PATENT DOCUMENTS 8,094,904 B2    1/2012  Slabaugh
8,233,692 B2    7/2012  Merlet
(Continued)

FOREIGN PATENT DOCUMENTS

WO    WO2011077334 A1    6/2011
WO    WO2014054018 A2    4/2014

OTHER PUBLICATIONS

Von Berg, J. et al., "A Novel Bone Suppression Method that Improves Lung Nodule Detection", Cross Mark, International Journal of Computer Assisted Radiology and Surgery, Apr. 2016, vol. 11, Issue 4, pp. 641-655|.

(Continued)

*Primary Examiner* — Leon Viet Q Nguyen
(74) *Attorney, Agent, or Firm* — Larry Liberchuk

(57) ABSTRACT

The present invention relates to an apparatus (10) for feature suppression in dark field or phase contrast X-ray imaging. The apparatus comprises an input unit (20), a processing unit (30) and an output unit (40). The input unit is configured to provide the processing unit with an X-ray attenuation image of a region of interest of an object. The input unit is also configured to provide the processing unit with a dark field or phase contrast X-ray image of the region of interest of the object. The processing unit is further configured to identify a first feature in the X-ray attenuation image; to identify a second anatomical feature in the X-ray attenuation image; and to identify the second anatomical feature in the dark field or phase contrast X-ray image. The first feature is an obscuring anatomical feature depicted in the X-ray attenu-
(Continued)

ation image with higher contrast than in the dark field or phase contrast X-ray image. The processing unit is also further configured to register the dark field or phase contrast X-ray image to the X-ray attenuation image based on the identified second anatomical feature. The processing unit is configured to determine a location of the first feature in the X-ray attenuation image; and to locate the first feature in the dark field or phase contrast X-ray image comprising utilization of information relating to the first feature identified in the X-ray attenuation image by transferring the determined location to the dark field or phase contrast X-ray image. The processing unit is still further configured to suppress the first feature in the dark field or phase contrast X-ray image to generate a feature suppressed dark field or phase contrast X-ray image. And the output unit is configured to output data representative of the feature suppressed dark field or phase contrast X-ray image.

11 Claims, 9 Drawing Sheets

(51) Int. Cl.
*A61B 6/00* (2006.01)
*G06T 7/73* (2017.01)
*G06T 7/33* (2017.01)
*G06T 3/00* (2006.01)

(52) U.S. Cl.
CPC .......... *A61B 6/5235* (2013.01); *G06T 3/0068* (2013.01); *G06T 5/50* (2013.01); *G06T 7/33* (2017.01); *G06T 7/74* (2017.01); *G06T 2207/10116* (2013.01); *G06T 2207/20056* (2013.01); *G06T 2207/30004* (2013.01); *G06T 2207/30008* (2013.01); *G06T 2207/30012* (2013.01); *G06T 2207/30061* (2013.01)

(58) Field of Classification Search
CPC . G06T 2207/20056; G06T 2207/30004; G06T 2207/30008; G06T 2207/30012; G06T 2207/30061; A61B 6/463; A61B 6/484; A61B 6/50; A61B 6/5235
See application file for complete search history.

(56) References Cited

U.S. PATENT DOCUMENTS

| 8,903,153 | B2 | 12/2014 | Von Berg |
| 2009/0087070 | A1* | 4/2009 | Slabaugh ................. G06T 5/20 382/132 |
| 2010/0220834 | A1 | 9/2010 | Heismann |
| 2010/0266188 | A1 | 10/2010 | Burns |
| 2012/0257810 | A1 | 10/2012 | Von Berg |
| 2014/0140603 | A1 | 5/2014 | Huo |
| 2015/0150529 | A1* | 6/2015 | Hoshino ................ A61B 6/505 378/36 |
| 2015/0187096 | A1 | 7/2015 | Baturin |

OTHER PUBLICATIONS

Hahn, D. et al., "Statistical Iterative Reconstruction Algorithm for X-Ray Phase-Contrast CT", Scientific Reports, vol. 5, Article No. 10452, Jun. 12, 2015, XP055234215.

* cited by examiner

FEATURE SUPPRESSION IN DARK FIELD OR PHASE CONTRAST X-RAY IMAGING

FIELD OF THE INVENTION

The present invention relates to an apparatus for feature suppression in dark field or phase contrast X-ray imaging, to a system for feature suppression in dark field or phase contrast X-ray imaging, and to a method for feature suppression in dark field or phase contrast X-ray imaging, as well as to a computer program element and a computer readable medium.

BACKGROUND OF THE INVENTION

Differential phase contrast and dark-field imaging are promising technologies that will likely add additional diagnostic value in particular in the area of chest imaging since these techniques are highly sensitive to changes of the micro-structure of lung tissue. In pre-clinical studies, it has been demonstrated that wide-spread lung diseases like chronic obstructive pulmonary disease (COPD) and fibrosis can be accurately identified and even quantified by this technology in mice. Still it remains open, how to build an operational system, such as a clinical system. However, features such as bones interfere with the imagery, which is exacerbated for larger subjects. Although features such as bones interfere with imagery, they are not depicted with sufficient contrast and signal to noise to enable their removal through image processing techniques.

WO2011/077334A1 relates to bone suppression in X-ray radiograms.

SUMMARY OF THE INVENTION

Therefore, it would be advantageous to have an improved technology for providing dark field or phase contrast images.

The object of the present invention is solved with the subject matter of the independent claims, wherein further embodiments are incorporated in the dependent claims. It should be noted that the following described aspects of the invention apply also for the apparatus for feature suppression in dark field or phase contrast X-ray imaging, system for feature suppression in dark field or phase contrast X-ray imaging and the method for feature suppression in dark field or phase contrast X-ray imaging, and for the computer program element and the computer readable medium.

According to a first aspect, there is provided an apparatus for feature suppression in dark field or phase contrast X-ray imaging, comprising:

an input unit;
a processing unit; and
an output unit.

The input unit is configured to provide the processing unit with an X-ray attenuation image of a region of interest of an object. The input unit is also configured to provide the processing unit with a dark field or phase contrast X-ray image of the region of interest of the object. The processing unit is configured to identify a first feature in the X-ray attenuation image. The first feature is an obscuring anatomical feature depicted in the X-ray attenuation image with higher contrast than in the dark field or phase contrast X-ray image. The processing unit is configured to identify a second anatomical feature in the X-ray attenuation image and to identify the second anatomical feature in the dark field or phase contrast X-ray image. The processing unit is further configured to register the dark field or phase contrast X-ray image to the X-ray attenuation image based on the identified second anatomical feature. The processing unit is also configured to determine a location of the first feature in the X-ray attenuation image. The processing unit is also configured to locate the first feature in the dark field or phase contrast X-ray image comprising utilization of information relating to the first feature identified in the X-ray attenuation image by transferring the determined location to the dark field or phase contrast X-ray image. The processing unit is also configured to suppress the first feature in the dark field or phase contrast X-ray image to generate a feature suppressed dark field or phase contrast X-ray image. The output unit is configured to output data representative of the feature suppressed dark field or phase contrast X-ray image.

In this manner, obscuring features can be removed from dark field or phase contrast images, which could not be removed from those images on the basis of those images alone. This is because in dark field or phase contrast images, obscuring features (such as bone) typically have less contrast and less signal to noise than in regular attenuation images, and cannot be suppressed directly to the required levels of fidelity. Therefore, the obscuring feature is identified in a regular attenuation X-ray image and this information is used to locate the obscuring feature (e.g., bone or bones such as one or more ribs) in the phase contrast or dark field image. Once the location of the obscuring features is known, standard algorithms, in a similar manner as carried out for attenuation images, can be applied to suppress the obscuring features in the dark field or phase contrast image.

In other words, for the example of a dark field or phase contrast image of a chest, the ribs can be removed from the image to result in an image the diffusion (or attenuation) coefficients of which only depend on the lung.

In other words, dark field and/or phase contrast imaging can be used to view structures that have similar absorption cross-sections, that would not be discernible using conventional absorption X-ray imaging, but in such dark field and/or phase contrast imaging the obscuring effects of features such as (for example) rib cage bones can be difficult to overcome. Therefore, the dark field and/or phase contrast image is associated with a conventional absorption X-ray of the same object, and in the absorption image the contrast between highly absorbing features such as bone and the adjacent relatively weakly absorbing material is greater than that for the dark field and/or phase contrast image. Therefore, the obscuring feature is identified in the attenuation "conventional" image, and this enables the same feature to be identified and located in the dark field and/or phase contrast image.

Having identified the location of the obscuring feature in the dark field and/or phase contrast image, using information from the attenuation image, the obscuring effect of the feature (e.g. rib cage bones) can be mitigated using state of the art techniques, for example in effect changing the properties of the bone to that of the surrounding body material. In this way, bone suppression algorithms can be applied to an attenuation image, and the resulting bone map (for the example of a body) that would be used for bone removal (or suppression) in the attenuation image is used for bone removal (suppression) in the dark field or phase contrast image.

In other words, the processing unit registers the dark field or phase contrast X-ray image to the X-ray attenuation image, and having registered the images and having identified the obscuring feature in the attenuation image, this information can be used to locate the first feature in the dark field or phase contrast X-ray image.

By registering the phase contrast or dark field image with the attenuation image, the obscuring feature identified in the attenuation image can be more easily located in the phase contrast or dark field image.

In other words, the first feature is located in the attenuation image and that location is transferred to the dark field or phase contrast X-ray image, thereby locating the obscuring feature in the dark field or phase contrast X-ray image.

In an example, the processing unit is configured to locate the first feature in the dark field or phase contrast X-ray image comprising utilization of information relating to the second feature identified in the attenuation image and identified in the dark field or phase contrast image.

In other words, a feature that is discernible in both the attenuation image and in the dark field or phase contrast image can be identified in both images, and because the obscuring feature has been identified in the attenuation image, information regarding the identified feature in both the attenuation and phase contrast/dark field image can be used to locate the obscuring feature in the dark field/phase contrast image.

In this manner, the obscuring feature can be more easily located in the phase contrast or dark field image.

In other words, a feature such as a lung is identified in the X-ray attenuation image, and the lung in also shown in a visible and distinct manner in the Dark Field or Phase Contrast image. A correlation between the visible lungs in both images can be made to locate the bones in the DF or PC image, that are not particularly visible, from the positions of the bones that are visible in the X-ray attenuation image.

According to an example, the processing unit is configured to determine information relating to a relative position of the first feature to the second feature in the X-ray attenuation image, and the processing unit is configured to determine a relative position of the first feature to the second feature in the dark field or phase contrast X-ray image on the basis of the information relating to the relative position of the first feature to the second feature in the X-ray attenuation image.

In other words, having identified for example a lung in both an attenuation image and a dark field or phase contrast image, then the relative position of for example a bone with respect to the lung in the attenuation image can be used such that the location of the bone in the dark field or phase contrast image is that where the bone has the same relative position with respect to the lung in the dark field or phase contrast image as it has in the attenuation image.

According to an example, the object is a body part and the second feature comprises one or more of, at least a part of a lung, at least a part of a diaphragm, and at least a part of a spine.

According to an example, the first feature comprises at least a part of a bone structure.

In this manner, the obscuring effects of bone in a dark field or phase contrast image of a body can be mitigated.

According to an example, the processing unit is configured to determine a product of a diffusion coefficient (or attenuation coefficient) and a distance for the first feature in the dark field or phase contrast X-ray image to suppress the first feature in the dark field or phase contrast X-ray image.

In other words, the X-ray attenuation is the product of an attenuation per unit length multiplied by a length. Thus, the attenuation provided by a feature such as a bone is the attenuation per unit length for a bone multiplied by the length the X-ray passes through the bone. Thus, having identified the first feature (such as a bone) the thickness of the bone through which an X-ray passes can be estimated. Then, the diffusion (or attenuation) coefficient for soft material surrounding the bone can be multiplied with the length through the bone to provide an effective attenuation for the bone, had it actually been comprised of such soft material. This information can be used to suppress the bone (first feature) in the dark field or phase contrast image.

In this manner, the obscuring feature can be made to appear like the material surrounding it. For example, for a rib bone surrounded by body flesh, the product of diffusion coefficient and length at the position of the rib bone can be replaced by that for the diffusion coefficient and length for the surrounding flesh. The rib bone will then appear to be the made from "flesh" rather than bone, and its obscuring effect will be mitigated.

According to an example, the processing unit is configured to determine a diffusion coefficient for the first feature and determine a distance comprising a length through the first feature in the dark field or phase contrast X-ray image. The processing unit is also configured to determine a diffusion coefficient for a feature other than the first feature in the dark field or phase contrast X-ray image. The processing unit is configured to replace the product of the diffusion coefficient for the first feature and the distance for the first feature with the product of the diffusion coefficient for the second feature and the distance for the first feature to suppress the first feature in the dark field or phase contrast X-ray image.

In this manner, for the example of a body, the suppression of the first feature can be considered as a virtual replacement of the bones in the body by soft tissue. In the dark field or phase contrast image, the bones will be made to disappear.

According to an example, the X-ray attenuation image and dark field or phase contrast X-ray image were acquired at substantially the same time.

In other words, the transmitted beam that passes through an object that is interrogated to produce a phase contrast or dark field image, can at the same time be used to produce an attenuation image.

In this manner, there is a direct correspondence between the attenuation image and dark field or phase contrast image, and having identified the obscuring feature in the attenuation image it can be easily located in the dark field or phase contrast image.

In a second aspect, there is provided a system for feature suppression in dark field or phase contrast X-ray imaging, the system comprising:

at least one image acquisition unit; and an apparatus for feature suppression in dark field or phase contrast X-ray imaging according to one of the above examples of an apparatus according to the first aspect. The at least one image acquisition unit is configured to provide the X-ray attenuation image, and to provide the dark field or phase contrast X-ray image. The output unit is configured to output the feature suppressed dark field or phase contrast X-ray image.

In a third aspect, there is provided a method for feature suppression in dark field or phase contrast X-ray imaging, comprising:

a) providing an X-ray attenuation image of a region of interest of an object;

b) providing a dark field or phase contrast X-ray image of the region of interest of the object;

c) identifying a first feature in the X-ray attenuation image;

d1) identifying a second anatomical feature in the X-ray attenuation image;

d2) identifying the second anatomical feature in the dark field or phase contrast X-ray image;
e) registering the dark field or phase contrast X-ray image to the X-ray attenuation image based on the identified second anatomical feature;
f) determining a location of the first feature in the X-ray attenuation image
g) locating the first feature in the dark field or phase contrast X-ray image comprising utilizing information relating to the first feature identified in the X-ray attenuation image by transferring the determined location to the dark field or phase contrast X-ray image;
h) suppressing the first feature in the dark field or phase contrast X-ray image to generate a feature suppressed dark field or phase contrast X-ray image; and
i) outputting data representative of the feature suppressed dark field or phase contrast X-ray image.

In an example, the first feature is a highly absorbing anatomical feature, for example bones.

In an example, the first feature is an anatomical feature, for example an obscuring feature, such as bones.

In an example, the first feature is depicted with higher contrast in the X-ray attenuation image than in the dark field or phase contrast X-ray image.

According to another aspect, there is provided a computer program element controlling apparatus as previously described which, in the computer program element is executed by processing unit, is adapted to perform the method steps as previously described. According to another aspect, there is provided a computer readable medium having stored computer element as previously described.

Advantageously, the benefits provided by any of the above aspects and examples equally apply to all of the other aspects and examples and vice versa.

The above aspects and examples will become apparent from and be elucidated with reference to the embodiments described hereinafter.

BRIEF DESCRIPTION OF THE DRAWINGS

Exemplary embodiments will be described in the following with reference to the following drawings.

DETAILED DESCRIPTION OF EMBODIMENTS

Figure 1:
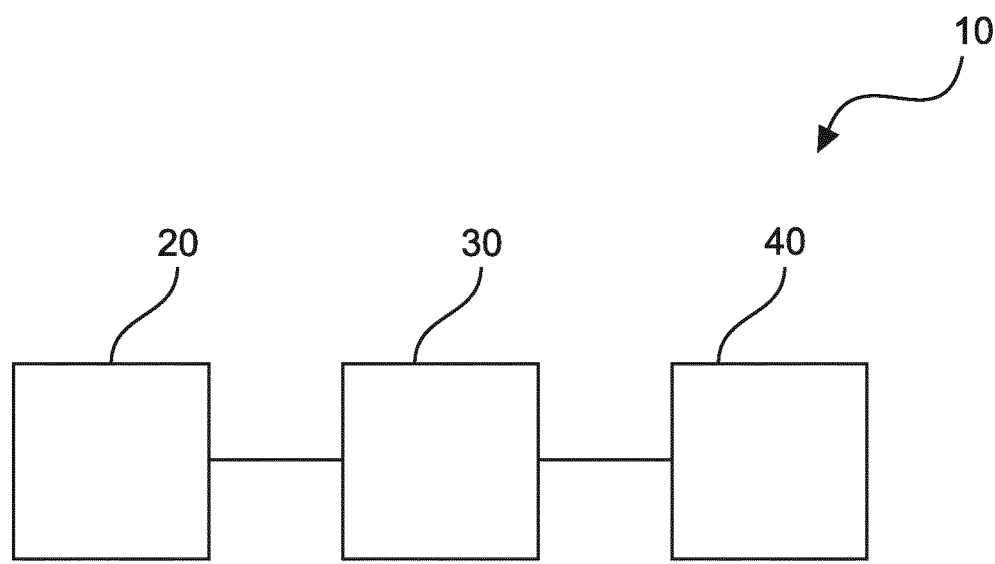
FIG. 1 shows an example of an apparatus for feature suppression in dark field or phase contrast X-ray imaging.

FIG. 1 shows an apparatus 10 for feature suppression in dark field or phase contrast X-ray imaging. The apparatus 10 comprises an input unit 20, a processing unit 30, and an output unit 40. The input unit 20 is configured to provide the processing unit 30 with an X-ray attenuation image of a region of interest of an object. The input unit 20 is also configured to provide the processing unit 30 with a dark field or phase contrast X-ray image of the region of interest of the object. The processing unit 30 is configured to identify a first feature in the X-ray attenuation image. The first feature is an obscuring anatomical feature depicted in the X-ray attenuation image with higher contrast than in the dark field or phase contrast X-ray image. The processing unit 30 is also configured to identify a second anatomical feature in the X-ray attenuation image; and to identify the second anatomical feature in the dark field or phase contrast X-ray image. The processing unit is further configured to register the dark field or phase contrast X-ray image to the X-ray attenuation image based on the identified second anatomical feature. The processing unit 30 is also configured to determine a location of the first feature in the X-ray attenuation image; and to locate the first feature in the dark field or phase contrast X-ray image comprising utilization of information relating to the first feature identified in the X-ray attenuation image by transferring the determined location to the dark field or phase contrast X-ray image. The processing unit 30 is also configured to suppress the first feature in the dark field or phase contrast X-ray image to generate a feature suppressed dark field or phase contrast X-ray image. The output unit 40 is configured to output data representative of the feature suppressed dark field or phase contrast X-ray image.

In an example, the X-ray attenuation image is a radiography image.

In an example, the X-ray attenuation image is an angiographic image.

In an example, identifying the first feature in the attenuation X-ray image means to identify the location of the first feature. In other words, a location of the first feature in the attenuation X-ray image is identified.

In an example, identifying the first feature in the attenuation X-ray image comprises application of a segmentation procedure.

In an example, locating the first feature in the dark field or phase contrast image comprises application of a segmentation procedure.

In an example, the first feature in the attenuation X-ray image is presented in a visible and distinct manner. The term "visible and distinct" relates to the first feature being presented such that at least a part of that first feature can be located and/or identified and/or delineated, either manually or automatically.

The processing unit 30 is configured to register the dark field or phase contrast X-ray image to the X-ray attenuation image.

In an example, registering accounts for the patient's cardiac cycle and/or breathing cycle.

In an example, registering may comprise the step of warping the region of interest of the attenuation image and/or the region of interest of the dark filed or phase contrast image.

In an example, acquisition of the attenuation image is performed at the same angulation as that used for acquisition of the dark image or phase contrast image. For example, both acquisitions are performed with the same C-arm angulation. This provides for ease of aligning the images.

In an example, the aligning leads to a spatial matching of the region of interest of the attenuation image with the region of interest of the dark field or phase contrast image.

In an example, registering the dark field or phase contrast image to the attenuation X-ray image comprises application of a segmentation procedure.

According to an example, the processing unit 30 is configured to determine a location of the first feature in the X-ray attenuation image and transfer that location to the dark field or phase contrast X-ray image.

In an example, locating the first feature in the attenuation X-ray image comprises application of a segmentation procedure.

According to an example, the processing unit 30 is configured to identify a second feature in the X-ray attenuation image. The processing unit is also configured to identify the second feature in the dark field or phase contrast X-ray image, and the processing unit is configured to locate the first feature in the dark field or phase contrast X-ray image comprising utilization of information relating to the second feature identified in the attenuation image and identified in the dark field or phase contrast image.

In an example, identifying the second feature in the attenuation X-ray image means to identify the location of the second feature. In other words, a location of the second feature in the attenuation X-ray image is identified. In an example, identifying the second feature in the dark field or phase contrast image means to identify the location of the second feature. In other words, a location of the second feature in the dark field or phase contrast image is identified. To put this another way, in an example, the processing unit is configured to locate the second feature in the X-ray attenuation image; and the processing unit is configured to locate the second feature in the dark field or phase contrast X-ray image.

In an example, the identified second feature in both the attenuation and phase contrast or dark field image is made use of in registering the phase contrast or dark field image to the attenuation image.

In an example, identifying the second feature in the attenuation X-ray image comprises application of a segmentation procedure. In an example, identifying the second feature in the dark field or phase contrast image comprises application of a segmentation procedure.

In an example, the second feature in the attenuation X-ray image is presented in a visible and distinct manner and the second feature in the Dark field or Phase Contrast image is presented in a visible and distinct manner. The term "visible and distinct" relates to the second feature being presented such that at least a part of that second feature can be located and/or identified and/or delineated, either manually or automatically.

According to an example, the processing unit 30 is configured to determine information relating to a relative position of the first feature to the second feature in the X-ray attenuation image. The processing unit is also configured to determine a relative position of the first feature to the second feature in the dark field or phase contrast X-ray image on the basis of the information relating to the relative position of the first feature to the second feature in the X-ray attenuation image.

According to an example, the object is a body part and the second feature comprises one or more of, at least a part of a lung, at least a part of a diaphragm, and at least a part of a spine.

According to an example, the first feature comprises at least a part of a bone structure.

According to an example, the processing unit 30 is configured to determine a product of a diffusion coefficient and a distance for the first feature in the dark field or phase contrast X-ray image to suppress the first feature in the dark field or phase contrast X-ray image.

According to an example, the processing unit 30 is configured to determine a diffusion coefficient for the first feature and determine a distance comprising a length through the first feature in the dark field or phase contrast X-ray image. The processing unit is also configured to determine a diffusion coefficient for a feature other than the first feature in the dark field or phase contrast X-ray image. The processing unit is further configured to replace the product of the diffusion coefficient for the first feature and the distance for the first feature with the product of the diffusion coefficient for the second feature and the distance for the first feature to suppress the first feature in the dark field or phase contrast X-ray image.

According to an example, the X-ray attenuation image and dark field or phase contrast X-ray image were acquired at substantially the same time.

Figure 2:
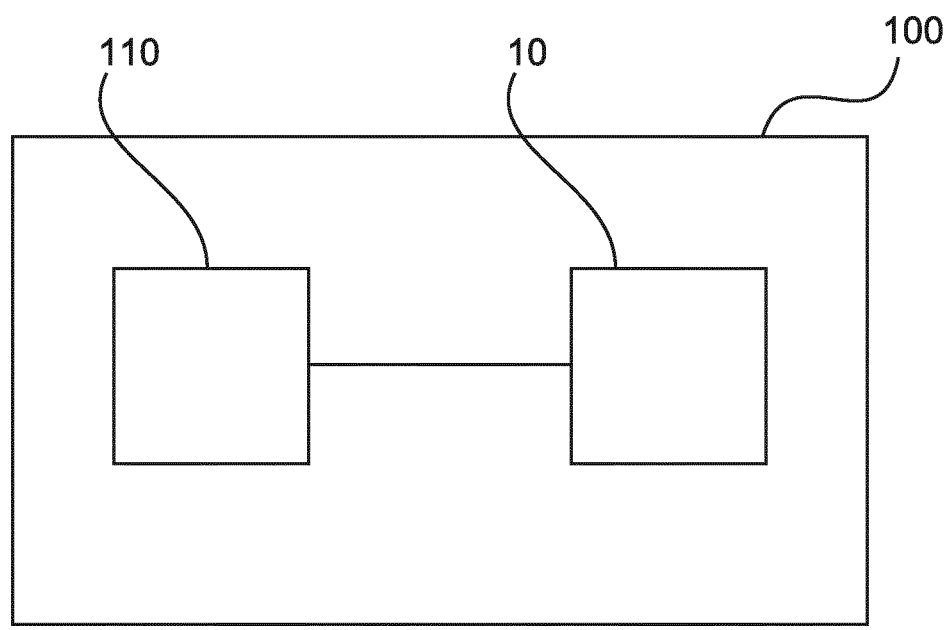
FIG. 2 shows an example of a system for feature suppression in dark field or phase contrast X-ray imaging.

FIG. 2 shows a system 100 for feature suppression in dark field or phase contrast X-ray imaging. The system 100 comprises at least one image acquisition unit 110, and an apparatus 10 for feature suppression in dark field or phase contrast X-ray imaging as described with respect to FIG. 1. The at least one image acquisition unit 110 is configured to provide the X-ray attenuation image, and to provide the dark field or phase contrast X-ray image. The output unit 40 is configured to output the feature suppressed dark field or phase contrast X-ray image.

In an example, the at least one image acquisition unit comprises a grating based differential phase contrast and dark field X-ray imaging device. In an example, the at least one image acquisition unit comprises an interferometer arrangement.

In an example, the at least one image acquisition unit comprises an X-ray imaging device. For example, the device can be a tomography arrangement, or a CT arrangement.

In an example, the at least one image acquisition unit can operate in a standard radiography mode, with transmitted intensities of radiation providing information on attenuation through the object. In an example, the at least one image acquisition unit can operate in a Differential phase contrast imaging (DPCI) mode. In an example, the same image acquisition unit can be used to acquire the attenuation and dark field or phase contrast images. For example, an interferometer arrangement of a DPCI apparatus can be swung out of the X-ray beam and a normal radiography, attenuation, image acquired. Then, the interferometer arrangement can be swung back into the X-ray beam and the dark field X-ray or phase contrast image acquired.

In an example, the at least one image acquisition unit comprises is a differential phase contrast imaging (DPCI) apparatus. In an example, the at least one image acquisition unit generates an attenuation image, relating to the detection of intensity (intensity) values of X-rays with and without the object in the examination region. In an example, the at least one image acquisition unit generates a phase contrast (or differential phase) image, relating to the detection of the phases of the X-rays with and without the object in the examination region. In an example, the at least one image acquisition unit generates a dark field (or de-coherence) image, relating to the detection of fringe visibilities of the X-rays with and without the object in the examination region. In an example, the at least one image acquisition unit generates any combination of these images. For example, the at least one image acquisition unit can generate an attenuation image, and generate a phase contrast image, and generate a dark field image. In an example, an attenuation image, a phase contrast image, and a dark field image can be generated at the same time.

In an example, the interferometer arrangement comprises a Talbot interferometer. In an example, the interferometer arrangement comprises a diffraction grating configured to modulate onto the X-rays emitted by the source an interference pattern detectable by the X-ray detector as X-ray fringes. In an example, the interferometer arrangement comprises a second diffraction grating configured to analyze the interference pattern. In an example, the second diffraction grating is an absorption grating. In an example, the two gratings are arranged on mutually opposite sides of an examination region. In an example, the two gratings are arranged on the same side of an examination region. In an example, the interferometer comprises a source grating in addition to the one or two gratings already discussed. In this example, the source grating is located relatively close to the X-ray source and serves to make the X-rays propagating after the source grating partly coherent. In other words, an X-ray source can be adapted so as to emit radiation that is more coherent than if the source grating was not present. Therefore, in some examples a source grating is not required, for example when the X-ray source already produces suitably coherent X-rays. In an example, the interferometer arrangement is configured to produce Moiré fringes. In an example, the interferometer arrangement is purposely detuned such that some fringes are present in a detector area. In an example, the interferometer arrangement is purposely detuned by having a first grating inclined at a small angle to a second grating. In an example, detuning leads to the generation of Moiré fringes on the detector.

In one example, the interferometer arrangement comprises two gratings which are fixedly mounted with respect to each other in a suitable frame or cage and this frame is fixedly arranged in a scan arm or other moveable gantry structure. In other words, the interferometer arrangement can be swung in and out of the X-ray beam such that the apparatus can be operated in both a DPCI mode and in a conventional radiography mode. In the DPCI mode, the arm can be translated or rotated, such that at least part of the object is scanned.

In an example, the output unit outputs an absorption (or attenuation) image. In an example, the output unit outputs a phase contrast (or differential phase) image. In an example, the output unit outputs a dark field image. In an example, the output unit outputs any combination of attenuation, phase contrast and dark field images. In other words, the output unit can simultaneously output all three types of image. In an example, the output unit outputs data representative of the object on a monitor such as a visual display unit or on a number of separate monitors. For example, attenuation, phase contrast and dark field images can be presented on a single monitor or presented on separate monitors.

In an example, the system has useful application in a clinical environment such as a hospital. In an example, the system can be used for mammography, diagnostic radiology and interventional radiology for the medical examination of patients. In an example, the system has useful application in an industrial environment, for example in non-destructive testing (e.g. analysis as to composition, structure and/or qualities of biological as well non-biological samples) as well as security scanning (e.g. scanning of luggage in airports). The apparatus has this application applicability too, as well as the method discussed below.

In an example, the fringe pattern generated at a current scan arm position is used to determine a visibility or mean visibility and at the same time is used to determine a transmission intensity of X-ray radiation at that arm position. In other words, an attenuation image can be acquired at the same time as a phase contrast and/or dark field image.

In an example, an image acquisition unit, such as a C-arm system, is used to acquire the attenuation image, and a different image acquisition unit, such as a DPCI system, is used to acquire the dark field and/or phase contrast image.

In an example, the object is a body or body part. In an example, the object is a piece of luggage or a part of a piece of luggage or a piece of luggage and its contents. In an example, the object is a part of an industrial device or machine part. In an example, the first feature is a bone. In an example, the first feature is a part of a piece of luggage such as a frame of a suitcase. In an example, the first feature is an item of apparel within a suitcase such as a sock or other item that is obscuring the contents of the suitcase. In an example, the second feature is a lung, a diaphragm or a part of the spine. In an example, the second feature is a part of the suitcase frame or other part of the luggage that is clearly discernible in both an attenuation image and dark field or phase contrast image (such as for example a shoe or shoes inside a suitcase).

Figure 3:
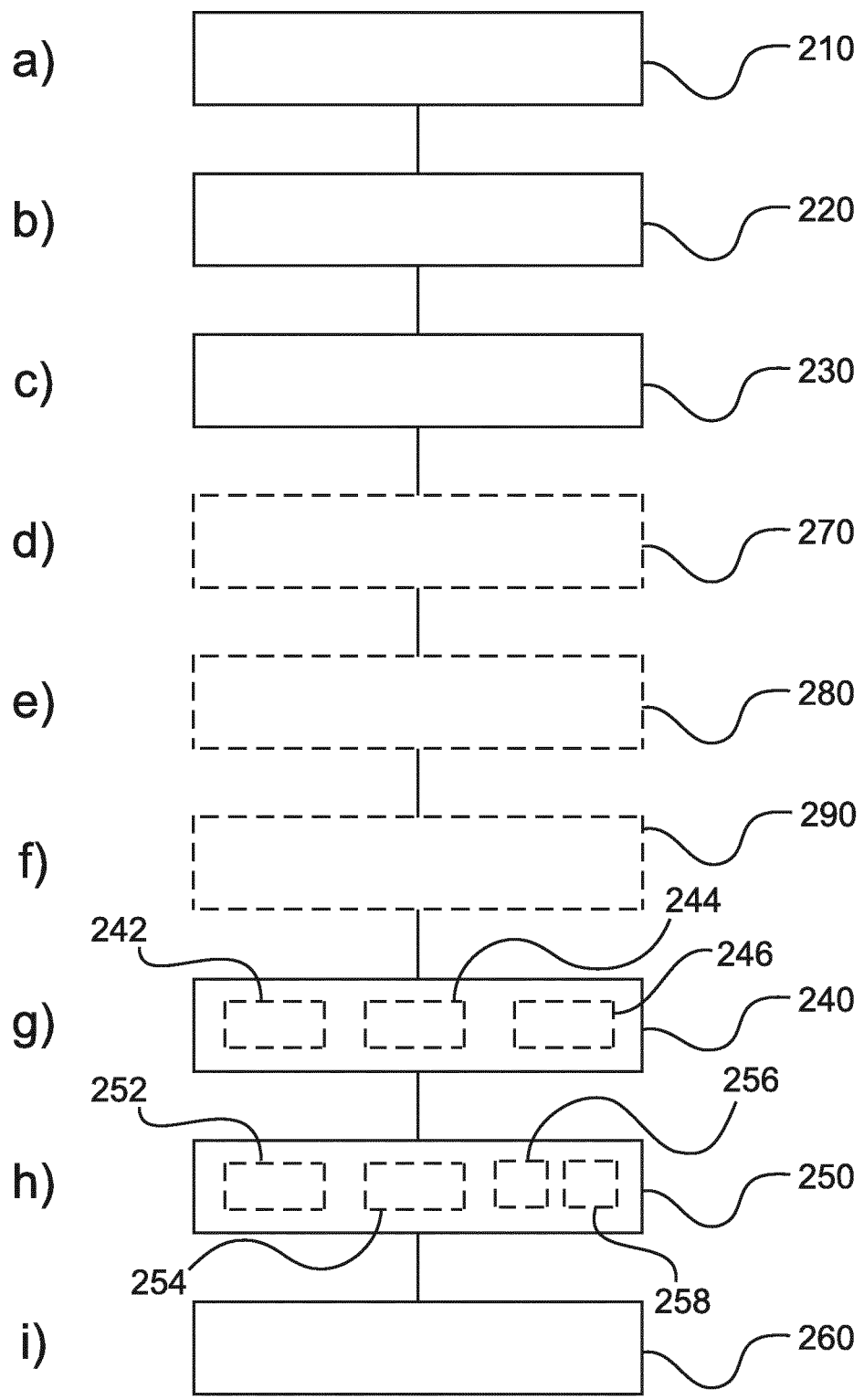
FIG. 3 shows an example of a method for feature suppression in dark field or phase contrast X-ray imaging.

FIG. 3 shows a method 200 for feature suppression in dark field or phase contrast X-ray imaging in its basic steps. The method 200 comprises:

in a providing step 210, also referred to as step a), an X-ray attenuation image of a region of interest of an object is provided;

in a providing step 220, also referred to as step b), a dark field or phase contrast X-ray image of the region of interest of the object is provided;

in an identifying step 230, also referred to as step c), a first feature in the X-ray attenuation image is identified;

in another identifying step 280, also referred to as step d1), a second anatomical feature is identified in the X-ray attenuation image;

in a further identifying step 290, also referred to as step d2), the second anatomical feature is identified in the dark field or phase contrast X-ray image;

in a registering step 270, also referred to as step e), the dark field or phase contrast X-ray image is registered to the X-ray attenuation image based on the identified second anatomical feature;

in a determining step 242, also referred to as step f), a location of the first feature in the X-ray attenuation image is determined;

in a locating step 240, also referred to as step g), the first feature in the dark field or phase contrast X-ray image is located comprising utilizing information relating to the first feature identified in the X-ray attenuation image by transferring the determined location to the dark field or phase contrast X-ray image;

in a suppressing step 250, also referred to as step h), the first feature in the dark field or phase contrast X-ray image is suppressed to generate a feature suppressed dark field or phase contrast X-ray image; and in an outputting step 260, also referred to as step i), data representative of the feature suppressed dark field or phase contrast X-ray image is output.

In an example, step g) comprises utilizing 244 information relating to the second feature identified in the attenuation image and identified in the dark field or phase contrast image.

In an example, step g) comprises determining 246 information relating to a relative position of the first feature to the second feature in the X-ray attenuation image, and determining a relative position of the first feature to the second feature in the dark field or phase contrast X-ray image on the basis of the information relating to the relative position of the first feature to the second feature in the X-ray attenuation image.

In an example, step h) comprises determining 252 a product of a diffusion coefficient and a distance for the first feature in the dark field or phase contrast X-ray image to suppress the first feature in the dark field or phase contrast X-ray image.

In an example, step h) comprises determining 254 a diffusion coefficient for the first feature and determining a distance comprising a length through the first feature in the dark field or phase contrast X-ray image; and determining 256 a diffusion coefficient for a feature other than the first feature in the dark field or phase contrast X-ray image; and replacing 258 the product of the diffusion coefficient for the first feature and the distance for the first feature with the product of the diffusion coefficient for the second feature and the distance for the first feature to suppress the first feature in the dark field or phase contrast X-ray image.

The apparatus, system and method for feature suppression in dark field or phase contrast X-ray imaging is now described in further detail with reference to FIGS. 4-15.

Figure 4:
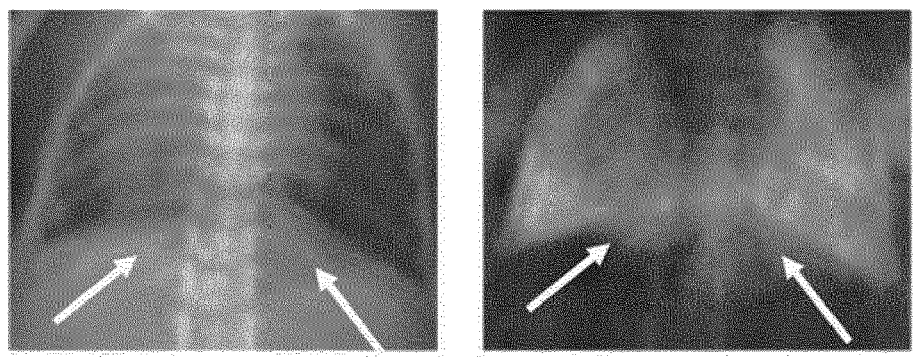
FIG. 4 shows on the left hand side an attenuation X-ray image and on the right hand side a dark field X-ray image for a mouse.

FIG. 4 shows an X-ray attenuation image on the left hand side and an associated dark field X-ray image on the right hand side for a mouse. The impact of the bones (ribs) in the dark-field image from mice is not great, because the bones are small, with the ribs only being visible below the diaphragm. However, for larger patients such as for humans the impact of the bones cannot be ignored. In regular attenuation images of human patients an X-ray energy of about 125 KV is used as the ribs have less contrast for high KV. However, dark-field imaging is more sensitive at lower x-ray energies, with X-ray energies of about 75 KV being used. The ribs become visible at these lower X-ray energies, to the extent that the bones interfere with the ability to analyze and interpret the dark-field image at these energies. The ribs also become more visible at these energies in the regular attenuation X-ray image.

Figure 5:
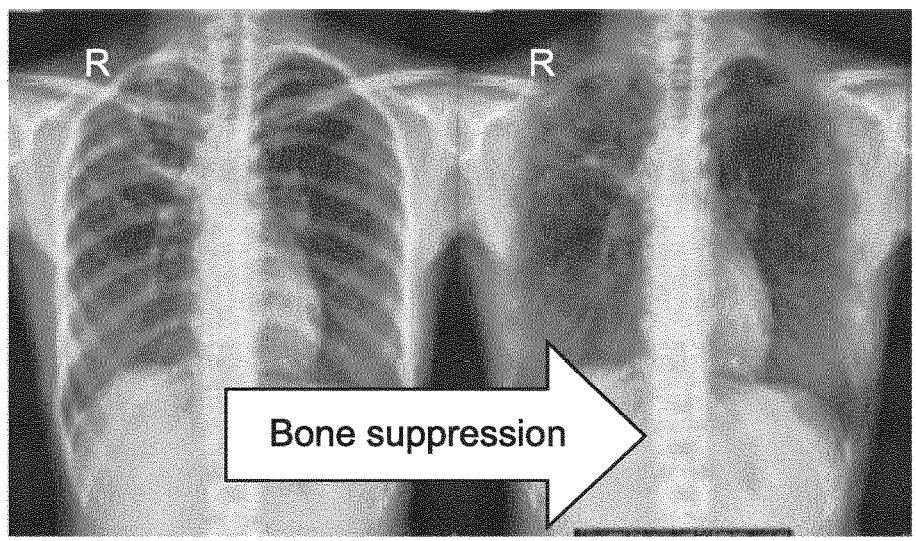
FIG. 5 shows an example of bone suppression in an X-ray image for a human, with FIG. 6 showing a schematic representation of FIG. 5.
Figure 6:
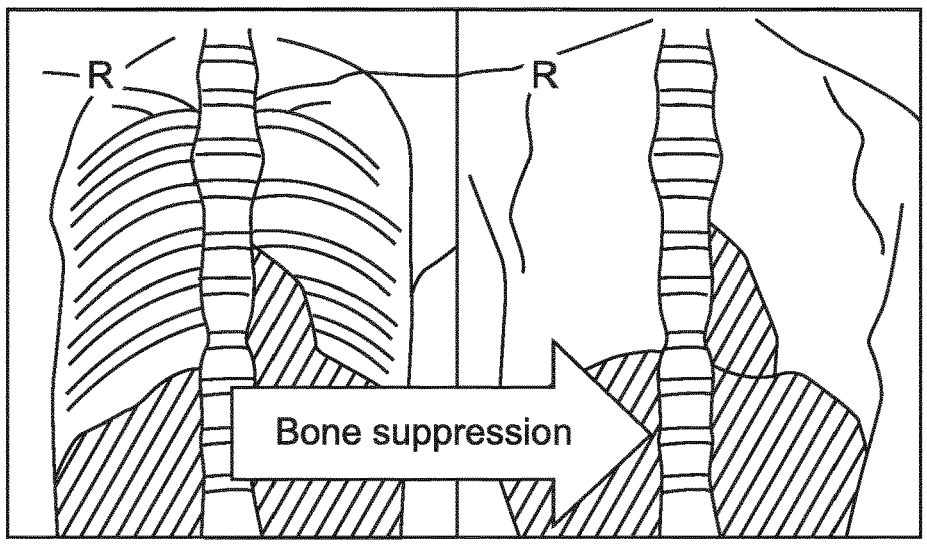

FIG. 5 Shows a regular X-ray attenuation image on the left-hand side, and on the right-hand side shows the X-ray attenuation image with bone suppression having been applied, for example through a technique as described in WO2011/077334A1. FIG. 6 shows in schematic form the imagery shown in FIG. 6.

Figure 7:
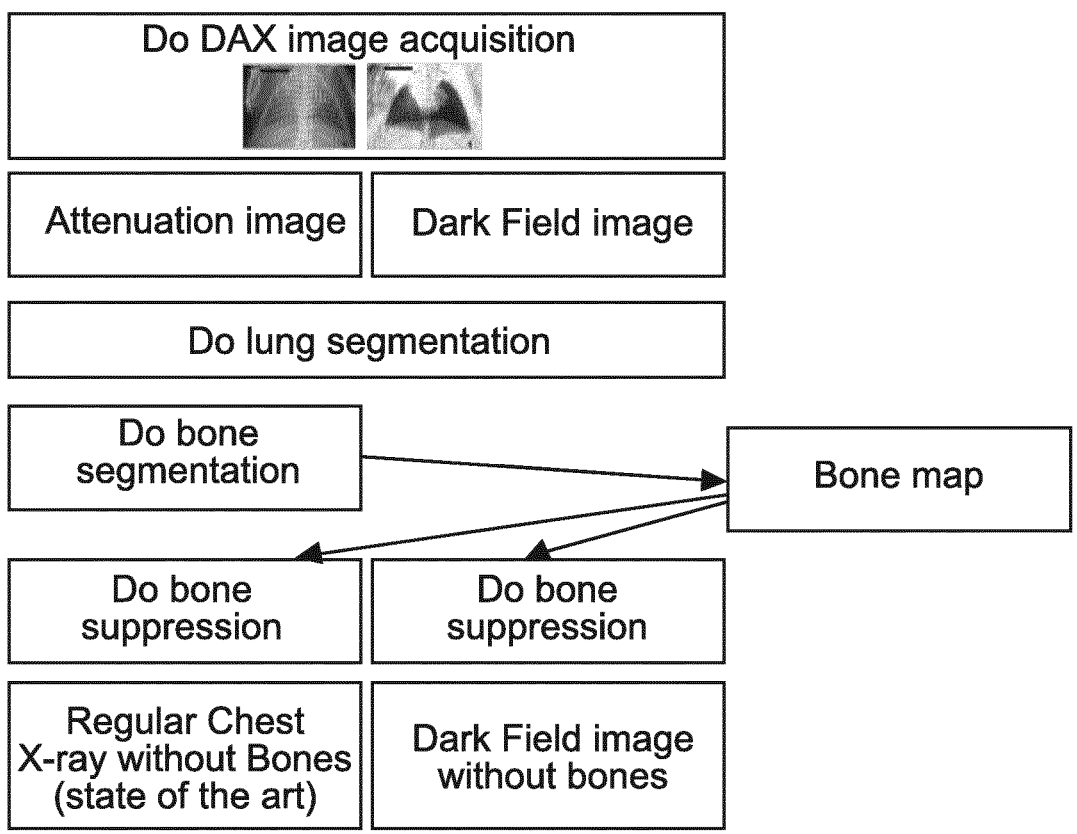
FIG. 7 shows a schematic representation of workflow for feature suppression in dark field or phase contrast X-ray imaging.
Figure 8:
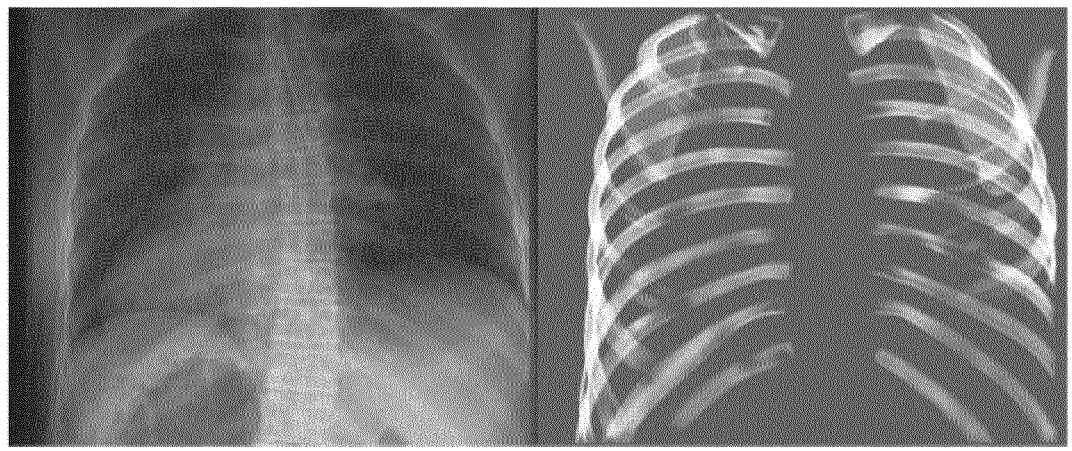
FIG. 8 shows on the left hand side an unprocessed attenuation X-ray image for a human, and on the right hand side the bones from this image, with FIG. 9 showing a schematic representation of FIG. 8.
Figure 9:
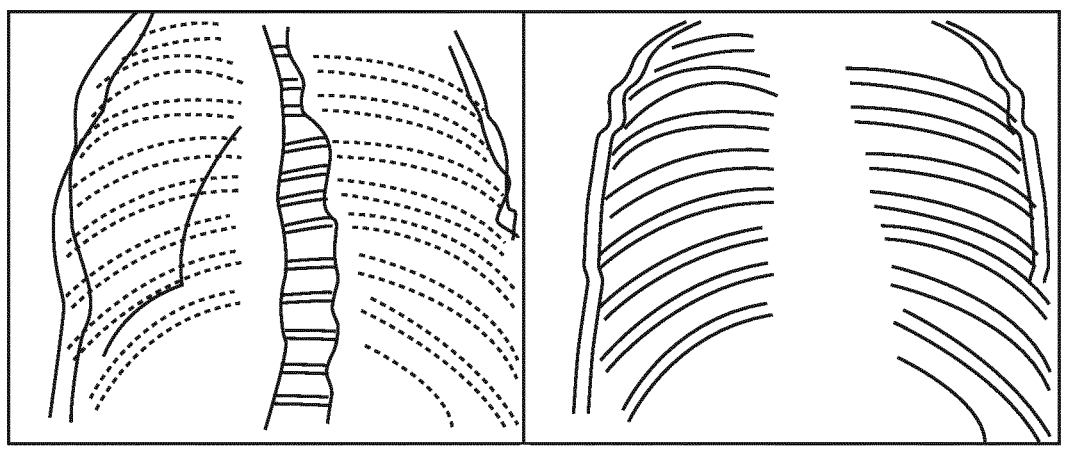

FIG. 7 shows a workflow for feature suppression in dark field or phase contrast X-ray imaging. An attenuation X-ray image of the chest is acquired, and an associated X-ray dark field (and/or phase contrast) image is acquired. The attenuation image and the dark-field image acquisition is described in more detail with respect to FIGS. 14 and 15, where it is to be noted and the attenuation image can be acquired at the same time or at different times to the dark field and/or phase contrast image. Lung segmentation is carried out for both the attenuation image and the dark-field image, using segmentation techniques as known in the art. This segmentation delineates the lungs in both images, and can also be used to register the attenuation image to the dark-field image, such that a region in the attenuation image can be mapped to the same region in the dark-field image. The bones in the x-ray attenuation image are clearly visible, as seen in the left hand image of FIG. 8 and its associated schematic representation in the left-hand diagram of FIG. 9. Segmentation of the bones in the X-ray attenuation image is then carried out. A bone map is then created, which is in effect that shown in the right image of FIG. 8 and its associated schematic representation in the right-hand diagram of FIG. 9. Bone suppression can then be carried out for the X-ray attenuation image as described for example in WO2011/077334A1. In effect the bones are removed in the image through a virtual replacement of the bones in the body by soft tissue, or by μBones>μSoft, where μ relates to X-ray attenuation. Having registered the attenuation image to the dark field image, the locations of the bones in the dark-field image can be determined on the basis of the bone map determined from the attenuation image, and this can be done even though the bones in the dark-field image of themselves not represented in that image with enough contrast of signal-to-noise to be delineated on the basis of just the dark-field image. Having identified the location of the bones in the dark-field image, a similar technique of bone suppression as applied to the X-ray attenuation image is now be applied to the dark-field image. The technique applied to the dark field image then suppresses the bones in the dark field image. In effect:

$$\ln(D) = [-\varepsilon \text{Lungs} * 1\text{Lungs} - \varepsilon \text{Soft}/1\text{soft} - \varepsilon \text{bones} * 1\text{bones}]$$

is transformed to $$[-\varepsilon \text{Lungs} * 1\text{Lungs} - \varepsilon \text{Soft} * 1\text{soft}]$$

Figure 10:
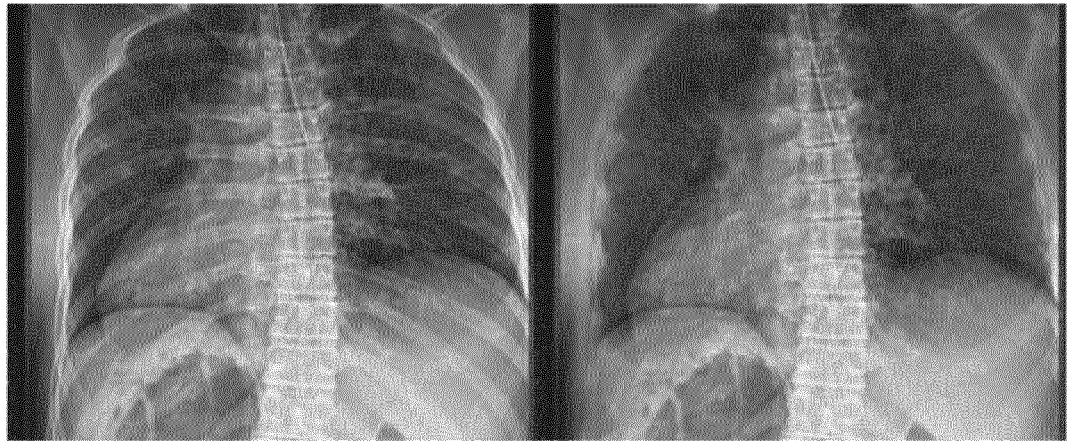
FIG. 10 shows on the left hand side an attenuation X-ray image for a human, and on the right hand side the attenuation image without bones, with FIG. 11 showing a schematic representation of FIG. 10.
Figure 11:
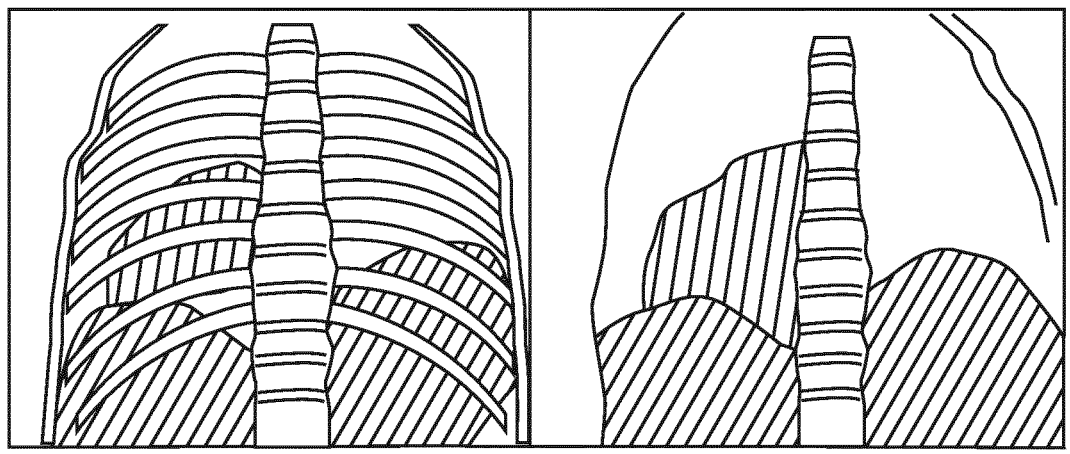

FIG. 10 shows on the left hand side an X-ray attenuation image showing bones, and on the right hand side the X-ray attenuation image having had bones suppressed as described above, with FIG. 11 showing a schematic representation of the images of FIG. 10.

Figure 12:
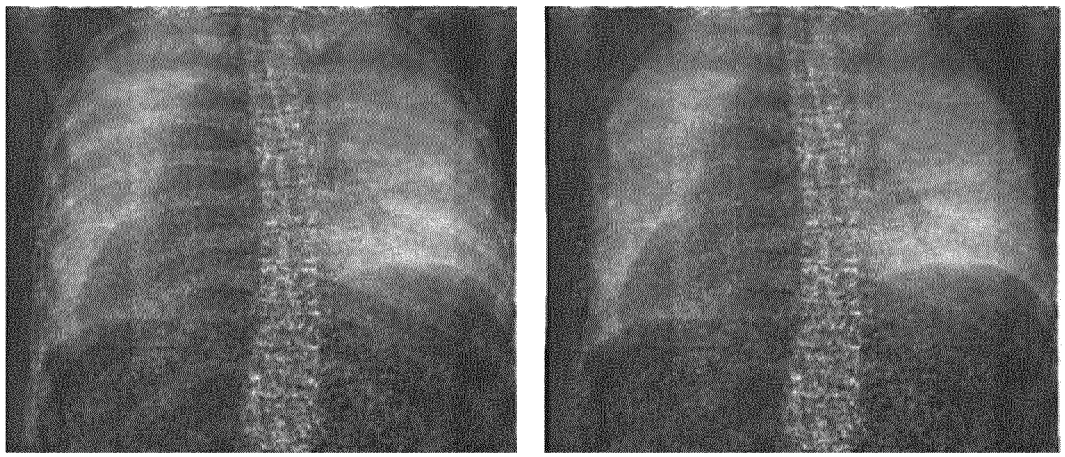
FIG. 12 shows on the left hand side an original dark field X-ray image for a human, and on the right hand side the dark field image with bones suppressed, with FIG. 13 showing a schematic representation of FIG. 12.
Figure 13:
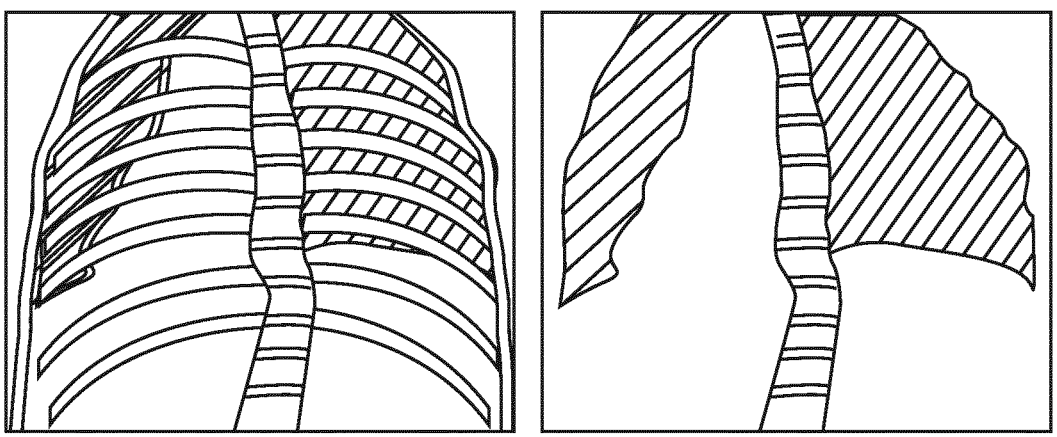

FIG. 12 shows on the left hand side an original dark field X-ray image showing bones, and on the right hand side the dark field X-ray image with bones having been suppressed as described above, with FIG. 13 showing a schematic representation of the images of FIG. 12.

Figure 14:
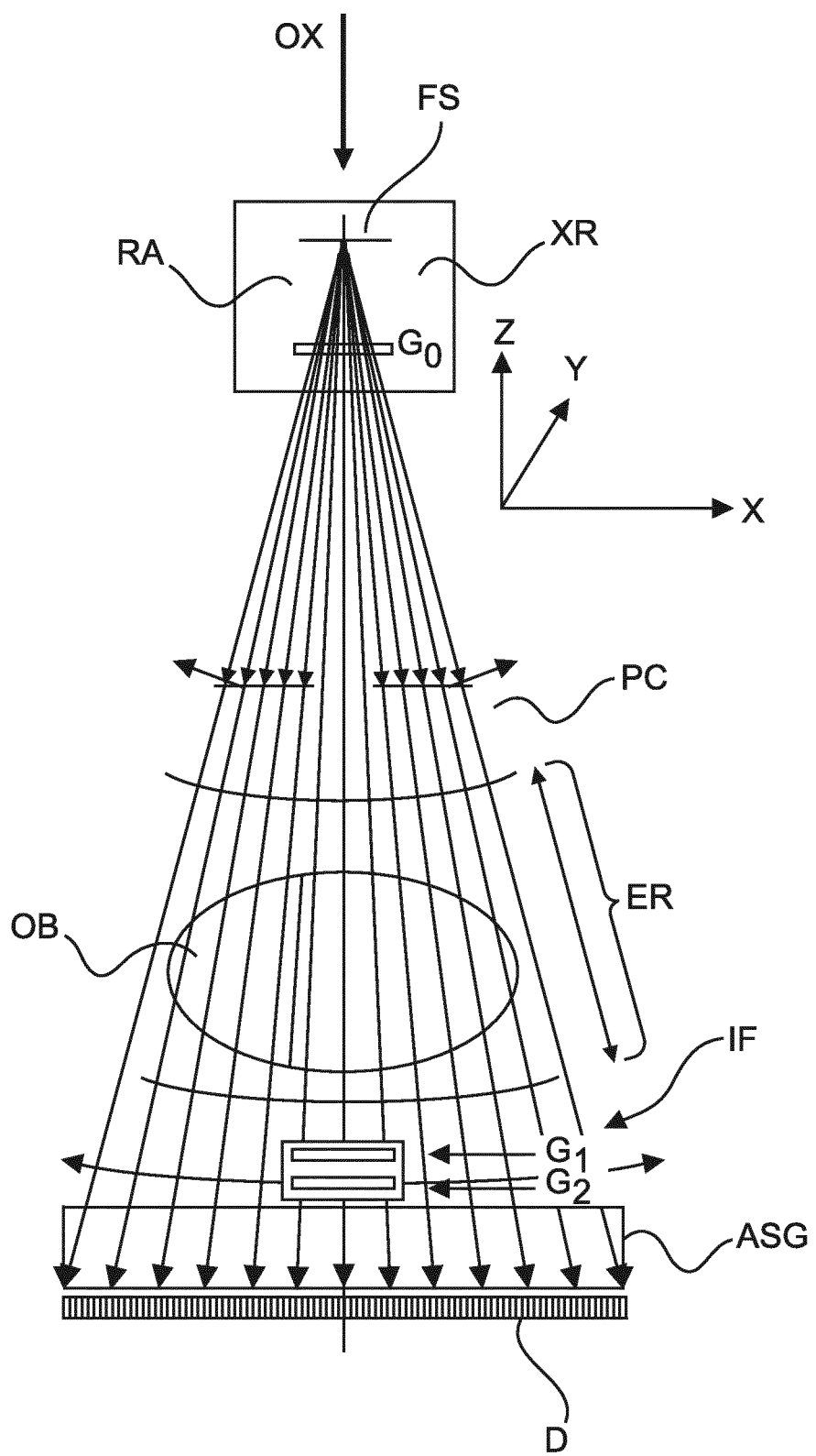
FIGS. 14-15 show schematic set ups of examples of a system for feature suppression in dark field or phase contrast X-ray imaging.

FIG. 14 shows an apparatus for acquiring the X-ray dark field and/or phase contrast images and that can also acquire X-ray attenuation images. The apparatus is capable of imaging for the spatial distribution of absorption of, or in, an object OB and also capable of imaging for the spatial distribution of refraction (phase contrast imaging) and also capable of imaging for the spatial distribution of small angle scattering (dark field imaging). The apparatus has a grating based interferometer IF that can be scanned across a stationary X-ray detector D. In this example, the interferometer IF comprises two grating structures G1 and G2 although, although in other examples a single grating interferometer (having only a single grating G1) is used. In the specific case of a single grating interferometer IF, the X-ray detector D has a pitch sufficiently small, hence a spatial resolution sufficiently large, for detecting i.e. adequately resolving the interference pattern generated by the grating G1 for the purpose of differential phase contrast imaging and/or dark field imaging. For that purpose the X-ray detector may be a high resolution X-ray detector, having for example a spatial resolution of 50 micrometers or more.

In FIG. 14, the grating G1 is either an absorption grating or phase shift grating whereas G2 is an absorption gating. The gratings are manufactured by photo lithographically processing suitable substrates such as a silicon wafer. A pattern of periodic rulings is formed in those silicon "cards" formed by trenches of different aspect ratio. The ruling patterns may be one dimensional but may also be two dimensional such as to confer a checker board pattern.

The X-ray imaging apparatus further comprises an X-ray source XR and the X-ray detector D. The X-ray detector D can be a 2D full view X-ray detector, which is either planar or curved. A plurality of detector pixels are arranged in rows and columns as an array to form a 2D X-ray radiation sensitive surface capable of registering X-ray radiation emitted by the X-ray source.

The X-ray detector D and the X-ray source are spaced apart to form an examination region ER. The examination region is suitably spaced to receive the object OB to be imaged. The object may be inanimate or animate. For instance the object may be a piece of luggage or other sample to be imaged, or in a medical context the object may be a human or animal patient or at least an anatomic part of a human or animal.

The interferometric grating structures G1 and G2 are arranged in the examination region ER between the X-ray source XR and X-ray detector D. The X-ray source XR has a focal spot FS from which the X-ray radiation beam emerges. It is the space between the focal spot FS and the X-ray detector's radiation sensitive surface where the two or three grating structures are arranged. The grating G1 is a phase grating and the grating G2 is an analyzer grating. In some embodiments, there is in addition to the interferometric gratings G1, G2 of the interferometer IF, a further grating G0 which is the source grating.

The source grating G0 is arranged in proximity of the X-ray source, for example at the exit window of a housing of the X-ray tube. The function of the source grating G0 is to make the emitted radiation at least partly coherent. In other words, the source grating G0 can be dispensed with if an X-ray source is used which is capable of producing coherent radiation.

In operation the at least partly coherent radiation passes through the examination region ER and interacts with the object OB. The object then modulates the attenuation, refraction, and small angle scattering information onto the radiation which can then be extracted by operation of the grating tandem G1 and G2. The gratings G1, G2 induce an interference pattern which can be detected at the X-ray detector D as fringes of a Moiré pattern. If there was no object in the examination region, there would still be an interference patter observable at the X-ray detector D, called the reference pattern which is normally captured during a calibration procedure. This comes about by especially adjusting or "de-tuning" the mutual spatial relationship between the two gratings G1 and G2 by inducing a slight flexure for instance so that the two gratings are not perfectly parallel. Now, if the object is positioned in the examination region and interacts with the radiation as mentioned, the Moiré pattern, which is now more appropriately called the object pattern, can be understood as a disturbed version of the reference pattern. This difference from the reference pattern can then be used to compute one or all of the three images (attenuation, phase contrast, dark field). This means that the attenuation image is acquired at the same time as the dark field and/or phase contrast image and as such the patient will be in the same state (e.g. breathing or other movement) and image registration is made more simple, enabling the location of the bones in the attenuation image to be transferred to locations in the dark field and/or phase contrast image. To be able to acquire suitable signals from which the images can be computed, a scanning motion is performed by the grating tandem G1-G2. As a result of this motion, at each pixel of the X-ray detector D a series of intensity values are detected. For good results, the detuning of the gratings G1, G2 is such that a period of the Moiré pattern should extend for a few of its cycles (two or three) in the direction of the scan motion. For each X-ray detector pixel, the series of intensity values can then be fitted to a (sinusoidal) signal forward model, for example, in order to derive the respective contributions of refraction, absorption, and small angle scatter. This type of signal processing is done in a signal processing unit not shown in FIG. 14, but which is known to the skilled person. The X-ray detector D remains stationary for any given orientation of the optical axis OX which is shown in FIG. 3 to extend along the Z axis. In other words, the X-ray detector D is kept stationary (at least during an image acquisition operation) with respect to an arbitrary reference point in the examination region. The interferometric setup as described above is what is commonly referred to as a Talbot-Lau interferometer. The distances between G0 and G1 and between G1 and G2 must be finely tuned to fit the requirements of Talbot distance which in turn is a function of the "pitch" (that is, the spatial period of the grating rulings) of the respective grating. Moving the interferometer IF relative to the X-ray detector D may cause a slight change in fringe distribution due to fringe drift. However, the fringe drift can be compensated by relating such drift to the fringe drift as obtained with a reference scan. Such reference scan may be a blank scan performed at the installation of the X-ray imaging apparatus.

The interferometer IF can be essentially a "grating pack" with the two gratings G1 and G2 fixedly mounted with respect to each other in a suitable frame or cage and this frame is fixedly arranged in a scan arm GT or other moveable gantry structure (not shown in FIG. 14). The arm, and with it the interferometer IF performs a pendulum like motion across the X-ray detector surface. The pivot point for the scan arm motion runs through the focal spot FS of the X-ray source but does not need to. The gratings G1 and G2 of the interferometer IF are held in fixed spatial relationship with respect to each other at all times during the scan motion and remain essentially parallel, or at least in a fixed spatial relationship, to G0. Suitable tracking circuitry (not shown) correlates interferometer position with X-ray detector pixel position to timely trigger a sequence of read-out burst to make sure each pixel is supplied with the above mentioned series of measurements to correctly sample the interference pattern.

In FIG. 14, the X-Y plane is the X-ray detector plane with X,Y designating the direction of pixelation in the X-ray detector D. The X-ray source rotates around the focal point that passes through the focal spot FS. The rotation axis RA for the scan arm GT and X-ray source XR extends into the paper plane of FIG. 14 (along the Y direction). Having the X-ray source rotate in concert with the pendulum motion of the grating tandem G1, G2 allows increasing flux.

In the example of FIG. 14, a pre-collimator is arranged between the X-ray source and the object OB so as to conform the radiation beam to the dimensions or footprint of the gratings G1 and/or G2. The collimator PC moves in concert with the pendulum motion of the interferometer IF during the image acquisition. One way to achieve this is to mount the collimator to the scan arm GT proximate to the source grating G0 at an appropriate distance. The source grating G0 also moves in concert with the swinging scanning motion of the grating pack G1, G2. One way to do this is to mount the grating in the scan arm. An anti-scatter grid ASG may be arranged between the interferometer and the X-ray detector surface.

In the example of FIG. 14 it is envisaged that the object, e.g. a patient, OB lies on an examination table or couch (not shown in FIG. 14) during the image acquisition. In other words the patient's longitudinal axis extends into the drawing plane as per FIG. 14 whilst the pendulum motion of the gratings G1, G2 (and that of G0) swings in a vertical plane with the patient's longitudinal axis (in FIG. 14 extending into the Y direction) extending into the paper plane of FIG. 14.

The mutually rigidly mounted gratings G1, G2 move the full length from one X-ray detector edge to the opposing X-ray detector edge if a full field image is desired, i.e. an image that is as wide in scan direction as the X-ray detector itself. If the user requests a smaller FOV (field of view), however, a reduced scan range can be used to minimize the acquisition time.

Figure 15:
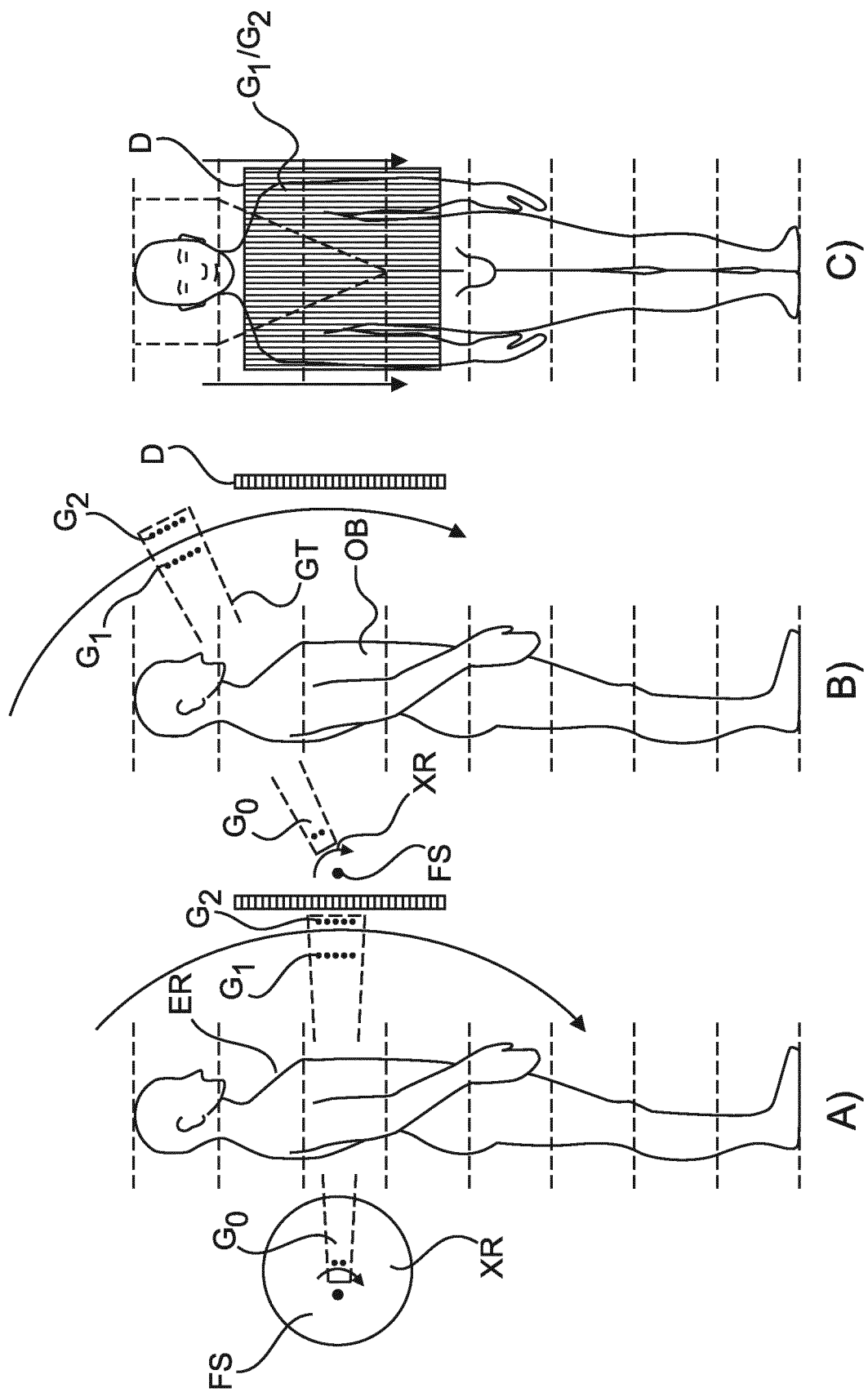

FIG. 15 shows a different example configured to allow the patient to stand (upright) during the X-ray imaging acquisition. This construction may be beneficial for chest imaging. Views A, B represent side elevations of the arrangement whilst view C is a frontal view through the X-ray detector D towards the X-ray source XR, that is, along the optical axis OX. Compared to FIG. 14 the optical axis in the FIG. 15 example is effectively rotated by 90 degrees. In other words the interferometer IF now performs a curved scan motion in a vertical direction (relative to the ground of the examination room) from top to bottom or from bottom to top. This is indicated in frontal view C by the arrows showing a (downward) movement of the interferometer IF during operation. Although not necessarily so in all examples, in FIG. 15 the gratings G1, G2 of the interferometer IF are now essentially arranged as strip gratings that are co-extensive of the width of the X-ray detector perpendicular to the scanning motion. Again, gratings G1, G2 may be formed monolithically from single long wafer or substrate. However, in other embodiments, the strip arrangement can be achieved by tiling, that is joining together a plurality of smaller individual monolithic grating modules. The X-ray detector may be suspended in a fixture from the ceiling of the examination room or may be mounted on a floor mounted stand. The gratings G1 and G2 are rigidly mounted to a scan arm GT. Equally, the scan arm GT may be floor or ceiling mounted. The side views A) and B) show different instances during the scanning motion of the scan arm GT as it is moving along the vertical scan path in a circular or at least arcuate motion. Again, although not necessarily in all embodiments, the source grating G1 is arranged to rotate in concert about the focal spot FS. One way to do this is to have all three gratings arranged in the scan arm to maintain a fixed and parallel relationship during the vertical up or down motion. In FIG. 15 parts that move simultaneously or in concert are shown in the dashed box representing the scan arm GT. The system can easily be operated in the conventional radiography mode, by simply moving the scan arm with the gratings out of the beam. If necessary, a standard chest X-ray image can be acquired immediately before the scan can be exploited by simply swinging the scan arm out of position.

In another exemplary embodiment, a computer program or computer program element is provided that is characterized by being configured to execute the method steps of the method according to one of the preceding embodiments, on an appropriate system.

The computer program element might therefore be stored on a computer unit, which might also be part of an embodiment. This computing unit may be configured to perform or induce performing of the steps of the method described above. Moreover, it may be configured to operate the components of the above described apparatus. The computing unit can be configured to operate automatically and/or to execute the orders of a user. A computer program may be loaded into a working memory of a data processor. The data processor may thus be equipped to carry out the method according to one of the preceding embodiments.

This exemplary embodiment of the invention covers both, a computer program that right from the beginning uses the invention and computer program that by means of an update turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An apparatus for feature suppression in dark field or phase contrast X-ray imaging, comprising:
   an input unit;
   a processing unit; and
   an output unit;
   wherein the input unit is configured to provide the processing unit with an X-ray attenuation image of a region of interest of an object;
   wherein the input unit is configured to provide the processing unit with a dark field or phase contrast X-ray image of the region of interest of the object;
   wherein the processing unit is configured to identify a first anatomical feature in the X-ray attenuation image; and to identify a second anatomical feature in the X-ray attenuation image; and to identify the second anatomical feature in the dark field or phase contrast X-ray image; wherein the first anatomical feature is an obscuring anatomical feature depicted in the X-ray attenuation image;
   wherein the processing unit is further configured to register the dark field or phase contrast X-ray image to the X-ray attenuation image based on the identified second anatomical feature;
   wherein the processing unit is configured to determine a location of the first anatomical feature in the X-ray attenuation image; and to locate the first anatomical feature in the dark field or phase contrast X-ray image comprising utilization of information relating to the first anatomical feature identified in the X-ray attenuation image by transferring the determined location to the dark field or phase contrast X-ray image;
   wherein the processing unit is configured to suppress the first anatomical feature in the dark field or phase contrast X-ray image to generate a feature suppressed dark field or phase contrast X-ray image; and
   wherein the output unit is configured to output data representative of the feature suppressed dark field or phase contrast X-ray image.

2. The apparatus according to claim 1, wherein the processing unit is configured to locate the first anatomical feature in the dark field or phase contrast X-ray image comprising utilization of information relating to the second anatomical feature identified in the attenuation image and identified in the dark field or phase contrast image.

3. The apparatus according to claim 2, wherein the processing unit is configured to determine information relating to a relative position of the first anatomical feature to the second anatomical feature in the X-ray attenuation image, and the processing unit is configured to determine a relative position of the first anatomical feature to the second anatomical feature in the dark field or phase contrast X-ray image on the basis of the information relating to the relative position of the first anatomical feature to the second anatomical feature in the X-ray attenuation image.

4. The apparatus according to claim 2, wherein the object is a body part and the second anatomical feature comprises one or more of, at least a part of a lung, at least a part of a diaphragm, and at least a part of a spine.

5. The apparatus according to claim 1, wherein the first anatomical feature comprises at least a part of a bone structure.

6. The apparatus according to claim 1, wherein the processing unit is configured to determine a product of a diffusion coefficient and a distance for the first anatomical feature in the dark field or phase contrast X-ray image to suppress the first anatomical feature in the dark field or phase contrast X-ray image.

7. The apparatus according to claim 6, wherein the processing unit is configured to determine a diffusion coefficient for the first anatomical feature and determine a distance comprising a length through the first anatomical feature in the dark field or phase contrast X-ray image; and wherein the processing unit is configured to determine a diffusion coefficient for a feature other than the first anatomical feature in the dark field or phase contrast X-ray image; and wherein the processing unit is configured to replace the product of the diffusion coefficient for the first anatomical feature and the distance for the first anatomical feature with the product of the diffusion coefficient for the second anatomical feature and the distance for the first anatomical feature to suppress the first feature in the dark field or phase contrast X-ray image.

8. The apparatus according to claim 1, wherein the X-ray attenuation image and dark field or phase contrast X-ray image were acquired at substantially the same time.

9. A system for feature suppression in dark field or phase contrast X-ray imaging, the system comprising:
   at least one image acquisition unit; and
   an apparatus for feature suppression in dark field or phase contrast X-ray imaging, comprising:
      an input unit;
      a processing unit; and
      an output unit;
      wherein the input unit is configured to provide the processing unit with an X-ray attenuation image of a region of interest of an object;
      wherein the input unit is configured to provide the processing unit with a dark field or phase contrast X-ray image of the region of interest of the object;
      wherein the processing unit is configured to identify a first anatomical feature in the X-ray attenuation image; and to identify a second anatomical feature in the X-ray attenuation image; and to identify the second anatomical feature in the dark field or phase contrast X-ray image; wherein the first anatomical feature is an obscuring anatomical feature depicted in the X-ray attenuation image;
      wherein the processing unit is further configured to register the dark field or phase contrast X-ray image to the X-ray attenuation image based on the identified second anatomical feature;
      wherein the processing unit is configured to determine a location of the first anatomical feature in the X-ray attenuation image; and to locate the first anatomical feature in the dark field or phase contrast X-ray image comprising utilization of information relating to the first anatomical feature identified in the X-ray attenuation image by transferring the determined location to the dark field or phase contrast X-ray image;
      wherein the processing unit is configured to suppress the first anatomical feature in the dark field or phase contrast X-ray image to generate a feature suppressed dark field or phase contrast X-ray image;
   wherein the at least one image acquisition unit is configured to provide the X-ray attenuation image, and to provide the dark field or phase contrast X-ray image; and wherein the output unit is configured to output the feature suppressed dark field or phase contrast X-ray image.

10. A method for feature suppression in dark field or phase contrast X-ray imaging, comprising:
- providing an X-ray attenuation image of a region of interest of an object;
- providing a dark field or phase contrast X-ray image of the region of interest of the object;
- identifying a first anatomical feature in the X-ray attenuation image;
- identifying a second anatomical feature in the X-ray attenuation image;
- identifying the second anatomical feature in the dark field or phase contrast X-ray image;
- registering the dark field or phase contrast X-ray image to the X-ray attenuation image based on the identified second anatomical feature;
- determining a location of the first anatomical feature in the X-ray attenuation image;
- locating the first anatomical feature in the dark field or phase contrast X-ray image comprising utilizing information relating to the first anatomical feature identified in the X-ray attenuation image by transferring the determined location to the dark field or phase contrast X-ray image;
- suppressing the first anatomical feature in the dark field or phase contrast X-ray image to generate a feature suppressed dark field or phase contrast X-ray image; and
- outputting data representative of the feature suppressed dark field or phase contrast X-ray image.

11. A non-transitory computer readable medium having one or more executable instructions stored thereon, which when executed by a processor, cause the processor to perform a method for feature suppression in dark field or phase contrast X-ray imaging, the method comprising:
- providing an X-ray attenuation image of a region of interest of an object;
- providing a dark field or phase contrast X-ray image of the region of interest of the object;
- identifying a first anatomical feature in the X-ray attenuation image;
- identifying a second anatomical feature in the X-ray attenuation image;
- identifying the second anatomical feature in the dark field or phase contrast X-ray image;
- registering the dark field or phase contrast X-ray image to the X-ray attenuation image based on the identified second anatomical feature;
- determining a location of the first anatomical feature in the X-ray attenuation image;
- locating the first anatomical feature in the dark field or phase contrast X-ray image comprising utilizing information relating to the first anatomical feature identified in the X-ray attenuation image by transferring the determined location to the dark field or phase contrast X-ray image;
- suppressing the first anatomical feature in the dark field or phase contrast X-ray image to generate a feature suppressed dark field or phase contrast X-ray image; and
- outputting data representative of the feature suppressed dark field or phase contrast X-ray image.

\* \* \* \* \*